(12) United States Patent
Weaver, II (10) Patent No.: US 9,278,021 B2
(45) Date of Patent: Mar. 8, 2016

(54) ORTHOPEDIC PRESSURE DEVICE

(75) Inventor: Edward L. Weaver, II, Milford, OH (US)

(73) Assignee: 3M Innovative Properties Company, Saint Paul, MN (US)

( * ) Notice: Subject to any disclaimer, the term of this patent is extended or adjusted under 35 U.S.C. 154(b) by 399 days.

(21) Appl. No.: 13/431,693

(22) Filed: Mar. 27, 2012

(65) Prior Publication Data

US 2012/0253252 A1 Oct. 4, 2012

Related U.S. Application Data

(60) Provisional application No. 61/468,697, filed on Mar. 29, 2011.

(51) Int. Cl.
*A61F 5/32* (2006.01)
*A61F 5/01* (2006.01)
*A61F 5/34* (2006.01)
*A61H 1/00* (2006.01)

(52) U.S. Cl.
CPC .............. *A61F 5/0118* (2013.01); *A61F 5/32* (2013.01); *A61F 5/34* (2013.01); *A61H 1/008* (2013.01); *A61H 2201/164* (2013.01); *A61H 2201/165* (2013.01); *A61H 2201/1635* (2013.01); *A61H 2205/06* (2013.01); *A61H 2205/104* (2013.01)

(58) Field of Classification Search
CPC ....... A61F 5/0106; A61F 5/0118; A61F 5/30; A61F 5/32; A61B 17/132; A61B 17/1322; A61B 17/1325; A61B 17/1327

USPC ............. 602/5, 16, 20–21, 23, 26, 62; 128/106.1, 112.1; 606/201–204
See application file for complete search history.

(56) References Cited

U.S. PATENT DOCUMENTS

| | | | |
|---|---|---|---|
| 6,228,103 | B1 | 5/2001 | Grey |
| 6,994,682 | B2 | 2/2006 | Bauerfeind |
| 7,618,386 | B2 | 11/2009 | Nordt, III |
| 7,780,612 | B2 | 8/2010 | Ross |
| 2003/0187375 | A1 | 10/2003 | Gaylord |
| 2004/0153065 | A1 | 8/2004 | Lim |
| 2006/0015980 | A1* | 1/2006 | Nordt et al. ................ 2/16 |
| 2006/0020237 | A1 | 1/2006 | Nordt |
| 2006/0095073 | A1 | 5/2006 | Beto |
| 2006/0156517 | A1 | 7/2006 | Hammerslag |
| 2006/0200057 | A1 | 9/2006 | Sterling |
| 2007/0169378 | A1 | 7/2007 | Sodeberg |
| 2007/0239092 | A1 | 10/2007 | Ross |
| 2008/0039765 | A1* | 2/2008 | Nordt et al. ............. 602/60 |
| 2008/0066272 | A1 | 3/2008 | Hammerslag |
| 2009/0043168 | A1* | 2/2009 | Parambil ................ 600/203 |

(Continued)

OTHER PUBLICATIONS

International Search Report for PCT/US12/30714 prepared by the ISA/US, Alexandria, Virginia, mailed Sep. 20, 2012.

*Primary Examiner* — Victoria J Hicks
*Assistant Examiner* — Kari Petrik
(74) *Attorney, Agent, or Firm* — Kevin Weber (57) ABSTRACT

An orthopedic pressure device comprises (a) a semi-rigid or rigid main body configured to contour the curvature of a portion of a wearer's anatomy, (b) an adjustable strap for securing the main body to the wearer, and (c) a displacing mechanism disposed in the main body for applying perpendicular force to the soft tissues of the wearer. The displacing mechanism comprises a lace and tensioning system for adjusting the perpendicular force to the soft tissues.

26 Claims, 5 Drawing Sheets

(56) References Cited

U.S. PATENT DOCUMENTS

2009/0287124 A1 11/2009 Shmidan
2010/0100120 A1 4/2010 Perkins
2010/0125231 A1 5/2010 Knecht
2010/0331750 A1 12/2010 Ingimundarson

* cited by examiner

ORTHOPEDIC PRESSURE DEVICE

CROSS REFERENCE TO RELATED APPLICATION

This application claims the benefit of U.S. Provisional Patent Application No. 61/468,697, filed Mar. 29, 2011, the disclosure of which is incorporated by reference herein in its entirety.

FIELD

This invention relates to orthopedic pressure devices for providing localized perpendicular force to portions of a wearer's anatomy.

BACKGROUND

Localized compression is useful in the prevention and treatment of various soft tissue symptoms and/or pathologies such as, for example, lateral epicondylitis ("tennis elbow"), medical epicondylitis ("golfer's elbow"), patellofemoral syndrome (PFS), chondramalacia patella (CMP), and the like. Most existing orthopedic devices, however, apply predominantly circumferential force to targeted soft tissue using, for example, an adjustable strap that encircles a body part with a pad. Therefore, many of these devices do not allow local perpendicular compression force adjustment to be made separately from and/or in addition to general circumferential force adjustment. This approach can create a tourniquet effect, which can become uncomfortable and cause tingling or numbness due to blood flow restriction.

Thus, approaches to provide orthopedic compression devices with reduced circumferential forces have been developed. U.S. Pat. No. 7,618,386, for example, uses a tensioning system to draw together two partial collars. A first partial collar is capable of applying a first force to a first side of an appendage and a second partial collar is capable of applying a second force to a second side of the appendage to apply generally opposing side-to-side tissue compression. This approach, however, does not allow for separate perpendicular compression force adjustment. U.S. Pat. No. 7,780,612 uses a threaded bolt assembly to provide adjustable perpendicular pressure to soft tissues.

SUMMARY

In view of the foregoing, we recognize that there is a need in the art for orthopedic compression devices that can provide adjustable focused perpendicular force to soft tissue. In addition, we recognize that it would be advantageous if such perpendicular force could be quickly and easily loosened and reapplied/retightened so that, depending upon the task at hand, users can adjust the perpendicular force accordingly.

Briefly, in one aspect, the present disclosure provides an orthopedic pressure device comprising (a) a semi-rigid or rigid main body configured to contour the curvature of a portion of a wearer's anatomy, (b) an adjustable strap for securing the main body to the wearer, and (c) a displacing mechanism disposed in the main body for applying perpendicular force to the soft tissues of the wearer. In particularly suitable aspects, the displacing mechanism comprises a lace and tensioning system for adjusting the perpendicular force to the soft tissues.

The pressure devices of the present disclosure thus meet the need in the art for pressure devices that provide adjustable, user-controlled, focused perpendicular force to soft tissue. Furthermore, in contrast to prior art devices, the displacing mechanisms of the disclosure provide a mechanical advantage to the pressure devices of the disclosure such that the amount of force input required is reduced. The tensioning system of the present disclosure can therefore be quickly and easily incrementally adjusted (i.e., loosened, tightened, removed, and/or reapplied) with little input force required so that the user can apply more (or less) perpendicular force as needed.

DETAILED DESCRIPTION

The orthopedic pressure devices of the disclosure include a semi-rigid or rigid main body that is configured to contour the curvature of a portion of a wearer's anatomy such as, for example, the wearer's back, shoulder, or an appendage. The main body can be, for example, in the general shape of a semicircle or a truncated semicircle. In some embodiments, for example, when the pressure device is being used on an appendage, the main body has a circumference from about 15 cm to about 50 cm. The circumference can vary depending upon the appendage on which the device will be worn (e.g., leg or arm) and the location on the appendage. In some embodiments, one or more ends of main body may include an area that curves slightly away from the appendage (i.e., a concave portion) so that the device may fit people with large appendages more comfortably. The main body can be constructed of any semi-rigid or rigid material. Preferably, it comprises a semi-rigid or rigid polymer such as nylon, polyoxymethylene (POM or "acetal"), polyethylene, polypropylene, acrylonitrile butadiene styrene (ABS), or the like. In some embodiments, the main body comprises a low friction material such as a lubricious polymer. The main body may optionally comprise padding (e.g., a foam or gel pad) on at least a portion of its inner surface for comfort.

The device also includes one or more adjustable straps for securing the main body to the appendage of the wearer. The strap is releasably engagable with the appendage. It typically comprises a flexible belt or strap that can be wrapped around the appendage and secured. The strap typically comprises a relatively inelastic material (for example, a material having no more than about 30% stretch under tension) such as foam laminates (for example, a laminate including polyester inner layer, urethane foam, and nylon jersey for exterior durability) or a woven cotton or nylon strap. The strap may also comprise an engaging surface similar, for example, to loop in a "hook and loop application" applied to either or both sides of the strap.

The strap should be long enough to reach securely around the appendage and is preferably wide enough to permit comfortable wear. The width of the strap can help to distribute the applied circumferential force around the wearer's appendage so the device held on firmly but still comfortable. Typically, the strap is between about 3.8 cm and about 6.4 cm wide. The width of the strap may vary.

The strap may be attached to the main body using various methods known in the art. For example, one end of the strap may be welded, glued or sewn to the main body while the other end can be removably attached to the main body using fastening structures such as buckles, snaps, slot buttons, or the like. In some embodiments, one or both ends of the main body comprise a slot or buckle through which an end of the strap may be passed and then secured with a closure tab comprising mating hook and loop materials.

The main body comprises a displacing mechanism disposed at least partially therein for applying perpendicular force to the soft tissue of the appendage or other areas of the wearer's anatomy on which the orthopedic pressure device is worn. The following description of the displacing mechanisms and various embodiments of the disclosure refer to applying pressure to the soft tissues of an appendage. It should be noted that the pressure devices of the disclosure can be used on other areas of a wearer's anatomy as well, and any reference to applying pressure to an appendage should not be interpreted to limit the scope or usefulness of the present disclosure.

The displacing mechanism may comprise padding where it contacts and applies perpendicular pressure to the appendage. The displacing mechanism comprises a lace and tensioning system for adjusting the perpendicular forces. The tensioning system includes a lace or cable that is threaded through or otherwise attached to a portion of the displacing mechanism and attached at opposite ends to a tightening or tensioning mechanism as described in further detail below.

The lace is preferably a low friction lace that slides relatively easily. The lace may be formed from any of a wide variety of polymeric or metal materials or combinations thereof that exhibit sufficient axial strength and bendability for the present application. For example, any of a wide variety of solid core wires, solid core polymers, or multi-filament wires or polymers, which may be woven, braided, twisted or otherwise configured, can be used. A solid or multi-filament metal core can be provided with a polymeric coating such as polytetrafluoroethylene (PTFE) or others known in the art in order to reduce friction. In one embodiment, the lace comprises a stranded cable such as a 7 by 7 strand cable manufactured of stainless steel. In order to reduce friction between the lace and the lace guides through which the lace slid, the outer surface of the lace is preferably coated with a lubricious material such as nylon or PTFE. In a preferred embodiment, the diameter of the lace ranges from about 0.024 inches to about 0.060 inches and is preferably 0.032 inches. The lace is desirably strong enough to withstand loads of at least about 40 pounds and preferably at least about 90 pounds. In certain embodiments, the lace is rated from about 100 pounds up to as high as about 200 pounds or more.

The tensioning mechanism is mounted to the main body. The tensioning mechanism can be located at any variety of locations on the brace. The shape and overall volume of the tensioning mechanism can be varied depending, for example, upon the gear train design. A relatively low-profile tensioning mechanism is generally preferred. The mounted profile of the tensioning mechanism can be further reduced by recessing the tensioning mechanism into the outer surface of the pressure device.

In general, the tensioning mechanism comprises a control such as a lever, crank or knob, which can be manipulated to retract the lace. Preferably, the tensioning mechanism is a rotary tensioning mechanism. In addition, the tensioning mechanism preferably comprises a mechanism of release such as a button or lever for disengaging the tensioning mechanism to permit the lace to be withdrawn freely. In some embodiments, the tensioning mechanism is released by pulling outwards on the control or by rotating the control knob counterclockwise. In some embodiments, an additional lock may be provided in the form of, for example, a button or lever that must be actuated to allow the control to be, for example, pulled outwards to release the system.

The tensioning mechanism generally comprises a housing and a circular knob rotatably mounted thereto. The knob may be rotated to wind the end of the lace into the housing and thereby provide the final tension to the lace to reduce the slack and provide the desired level of tightness or tension. The knob may also be rotated through the use of a tool or small motor attached to the knob. Examples of various tensioning mechanisms suitable for this task are disclosed in greater detail in U.S. Patent Publication Nos. 2006/0156517 and 2007/0169378. Suitable tensioning mechanisms are available from Boa Technology, Inc. (Steamboat Springs, Colo.).

Various configurations are possible for the displacing mechanism. Illustrative embodiments of displacing mechanisms of the disclosure will be explained below with reference to the drawings wherein similar reference characters denote similar elements throughout the various views and embodiments.

Figure 1A:
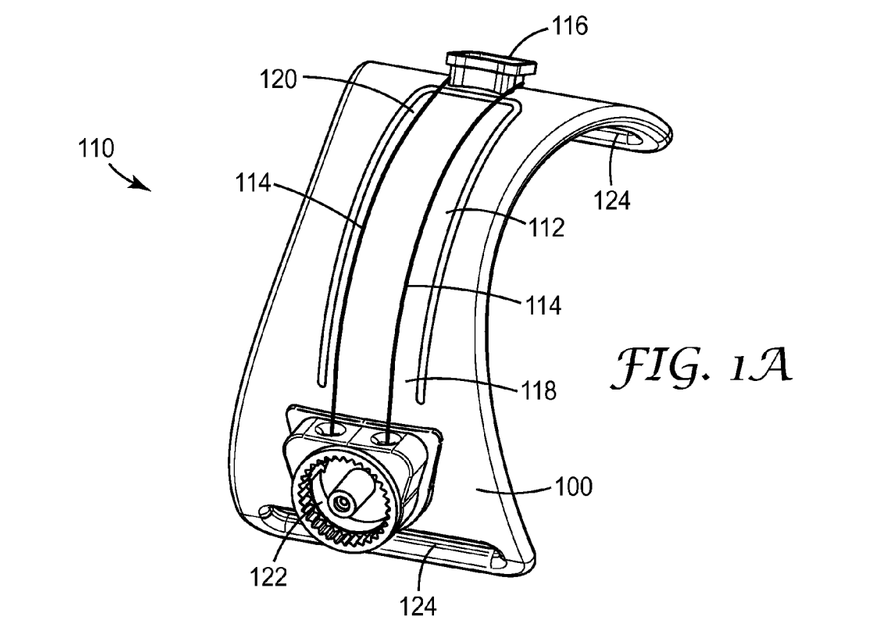
FIGS. 1A and 1B illustrate a displacing mechanism of the disclosure.
Figure 1B:
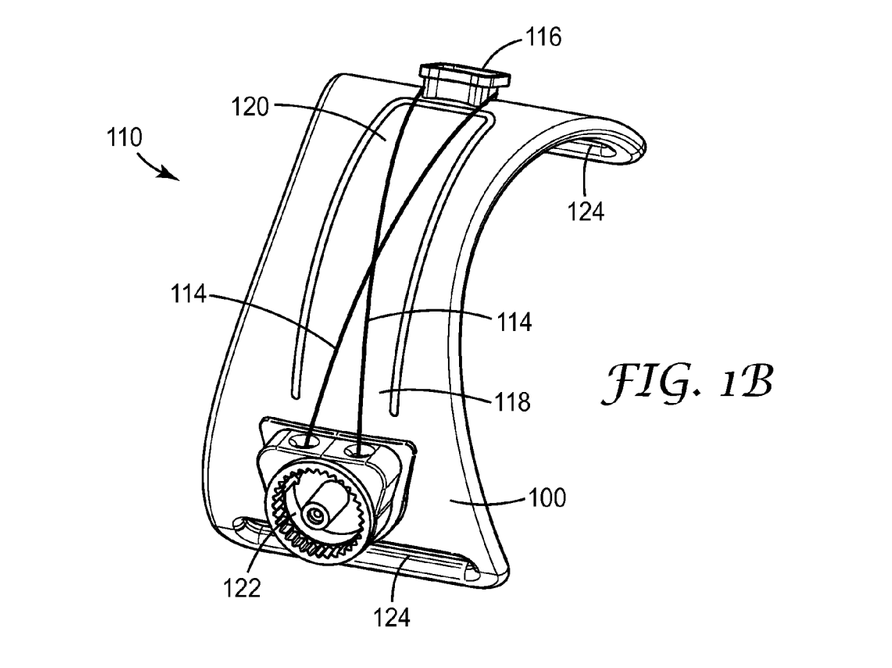

FIGS. 1A and 1B illustrate an embodiment of a displacing mechanism of the disclosure. Displacing mechanism 110 is disposed in main body 100. Displacing mechanism 110 comprises convexly curved flexible finger 112. Finger 112 includes connected end 118 and free end 120. Lace 114 runs over the outer surface of finger 112. Lace 114 is threaded through lace guide 116, which is located on the outer surface of main body 100 adjacent to free end 120, and attached at opposite ends to tensioning mechanism 122. Preferably, lace guide 116 is constructed of a rigid material that resists bending. Lace guides are also preferably constructed from low friction materials such as lubricious polymer or metal that facilitates sliding of the lace therethrough. Lace guides can be attached to the main body in any of a variety of ways or may be integral to the main body, as will be appreciated by those of skill in the art. Lace 114 may be threaded such that it crosses over finger 112 as shown in FIG. 1B. Alternatively, lace 114 may be threaded such that it runs parallel over finger 112 as shown in FIG. 1A.

When tension is applied to lace 114 using tensioning mechanism 122, finger 112 deflects or displaces under the tension. The perpendicular force focus is at free end 120 of finger 112; however, there may also be a more distributed force across the long axis of finger 112. Preferably, finger 112 is from about 2.5 cm to about 6.4 cm long.

Main body 100 can be secured to an appendage using an adjustable strap (not shown) that can attach to main body 100 at slots 124. In certain embodiments, a portion of the adjustable strap may be secured proximate the tensioning mechanism and can at least partially cover aspects of the displacement system, including e.g., the finger 112 and laces 114.

Figure 2:
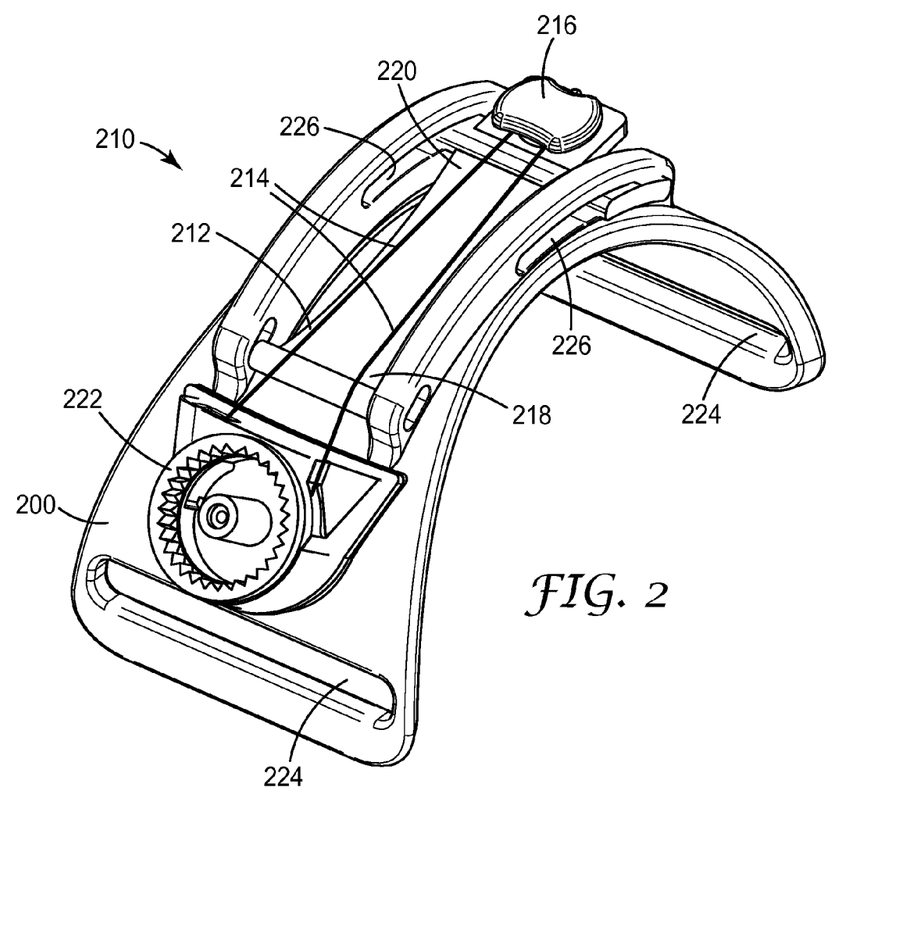
FIG. 2 illustrates another displacing mechanism of the disclosure.

FIG. 2 illustrates another embodiment of a displacing mechanism of the disclosure. In this embodiment, displacing mechanism 210 comprises concavely curved finger 212. Finger 212 includes first end 218, which is adjacent to tensioning mechanism 222, and second end 220, which is attached to lace 214 via lace guide 216. When lace 214 is tightened using tensioning mechanism 222, second end 220 of finger 212 slides along track 226 and finger 212 bows placing a downward force at the center of finger 212. Preferably, finger 212 is from about 2.5 cm to about 6.4 cm long.

Figure 4:
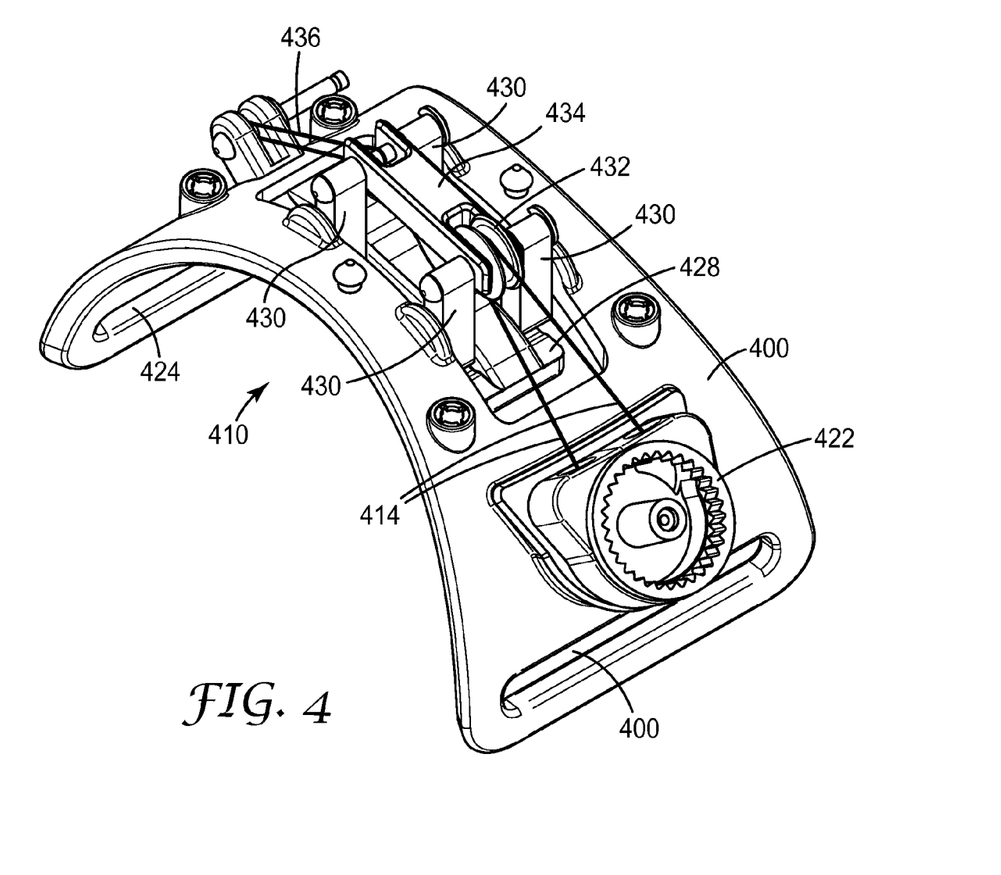
FIG. 4 illustrates another displacing mechanism of the disclosure.
Figure 5A:
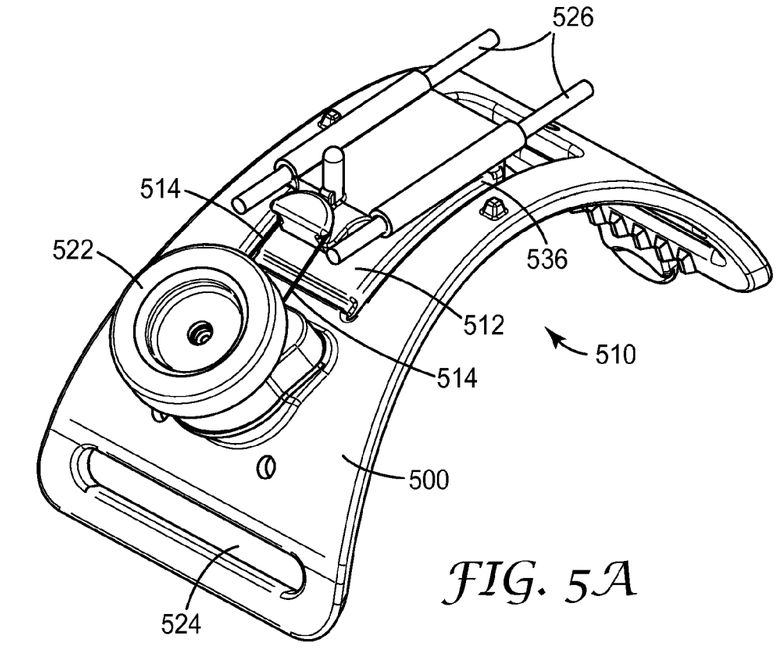
FIGS. 5A and 5B illustrates another displacing mechanism of the disclosure.
Figure 5B:
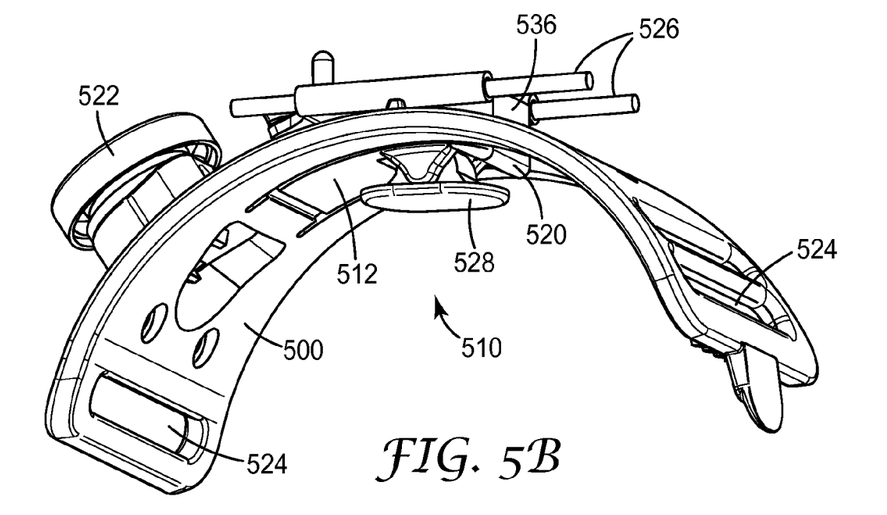

The displacing mechanisms shown in FIGS. 1A, 1B, 2 and 3 use line tension for displacing a cantilever arm, finger, or pad. If an opposing force is greater than the tension applied, the displacing mechanism will "give" or be allowed to lose vertical displacement. This approach may be preferred, for example, when treating areas that have very little soft tissue such as the patellar tendon. FIGS. 4 and 5 illustrate embodiments of displacing mechanisms of the disclosure wherein the displacing mechanisms convert torque force into linear force using a rigid mechanical positive displacement mechanism. These positive displacement mechanisms provide perpendicular force that will not allow for the cantilever arm or finger to "give" when encountering an opposing force. The forces will either equalize or, by design, can be overcome with an increased moment arm or more elongated wedge (as described below) with a different profile. Thus, if the opposing force is known, the positive displacement system can be designed to overcome the force with mechanical advantage providing a "non-forgiving" system.

Figure 3:
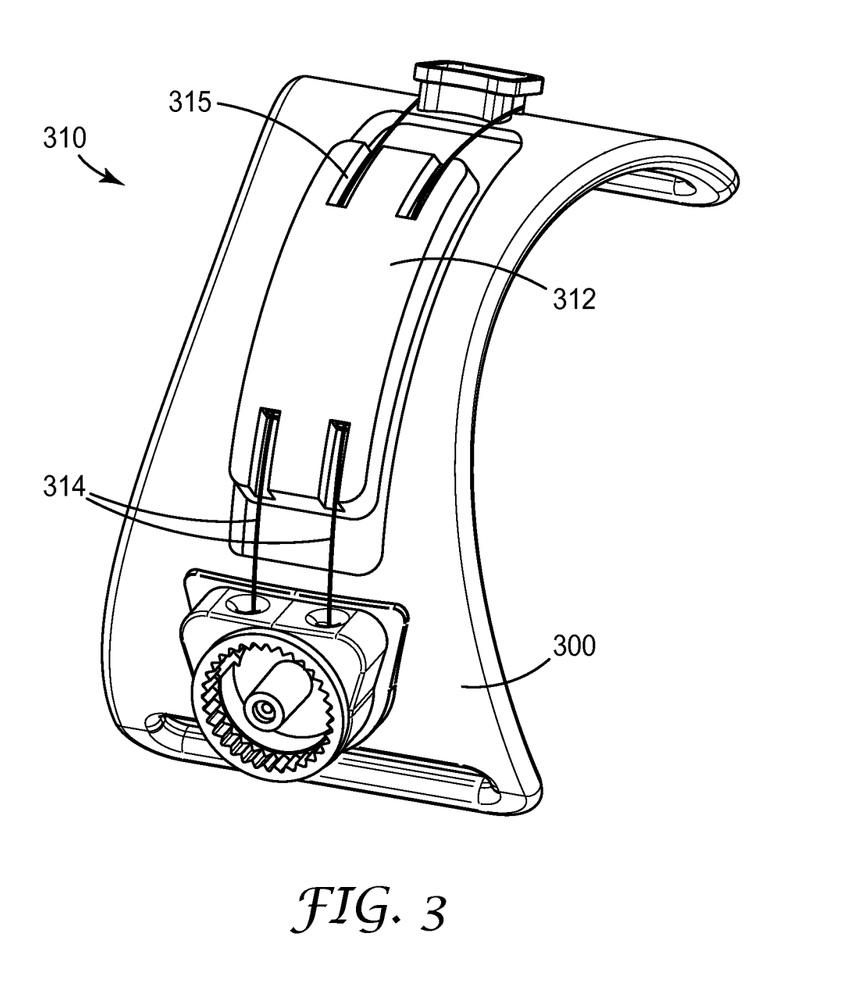
FIG. 3 illustrates another displacing mechanism of the disclosure.

In certain embodiments, as exemplified in FIG. 3, the displacing mechanism includes a pressure pad or foot 312 disposed at least partially within or proximate to the main body 300. The pressure pad 312 can be in lieu of or in addition to finger 112. The pad 312 may contour the curvature of a portion of a wearer's body, such that the pad 312 can also be convexly curved. The pressure pad 312 can be integral with the main body (e.g., coupled to finger 112) or can be the separable component 312 as shown in FIG. 3; the pad can also be rotatable or pivoting.

The lace 312 extends over at least a portion of the pad 312 surface and at least a portion of the pad 312 deflects or displaces under tension when tension is applied to the lace using the tensioning system. Accordingly, lace 314 can be coupled to and/or partially enclosed in the pad 312. For example, a pad 312 surface can include a trench 315 configured to releasably receive a portion of the lace 314. In other embodiments, the lace 314 can be coupled to the pad 312 via adhesive or other suitable fastening mechanism known in the art.

The pressure pad 312 typically includes a conformable and/or compressible material. Suitable materials are well known in the art (e.g., gel pads, foam, etc.). In certain aspects, the pressure pad 312 can be composed entirely of conformable and/or compressible material. Alternatively, the padding material can be secured to at least a portion of a surface of a rigid or semi-rigid pad body.

Rigid mechanical positive displacement mechanism 410, as shown in FIG. 4, includes pressure foot 428, which is rotatably connected to the bottom ends of rigid legs 430. Lace 414 is threaded through pulley 432 located on platform 434, which is rotatably connected to the top ends of rigid legs 430, and is attached at opposite ends to tensioning mechanism 422. Rigid legs 430 are positioned at an angle of less than 90° when lace 414 is not tensioned. Band 436 provides a slight pull on platform 434 in the opposite direction of tensioning mechanism 422. When lace 414 is tightened using tensioning mechanism 422, platform 434 is drawn toward tensioning mechanism 422 and rigid legs 430 rotate toward a 90° angle thus applying downward force at pressure foot 428.

Rigid mechanical positive displacement mechanism 510, as shown from two different perspectives in FIGS. 5A and 5B, utilizes convexly curved flexible finger 512 and rigid wedge 536, which slides along track 526. Finger 512 includes connected end 518 and free end 520. Rigid wedge 536 is spring-loaded (not shown) to pull in the direction opposite tensioning mechanism 522. When lace 514 is tightened using tensioning mechanism 522, wedge 536 is pulled toward tensioning mechanism 522 along track 526 thus deflecting finger 512 at free end 520 and applying downward force at pressure foot 528. Pressure foot 528 is rotatable or pivoting.

The orthopedic pressure devices of the disclosure use a displacing mechanism to provide adjustable, user-controlled, perpendicular compression to tissues without applying circumferential pressure to the appendage. The devices can be used for a variety of purposes including, for example, the treatment, amelioration, reduction, prevention, and/or control of muscle spasms, tendon tissue strain, tensile tissue stresses, repetitive strain, pain, tissue inflammation, peripheral nerve lesions, nausea, vomiting, morning sickness, motion sickness, local hematoma, local edema, and/or the like.

In use, the device is positioned on the wearer (e.g., a human or animal patient) such that area of the displacing mechanism that provides perpendicular force is aligned over the soft tissues to be compressed. The adjustable strap is then tensioned or engaged according to the patient's comfort, thereby securing the device onto the appendage of the wearer. The tensioning mechanism (e.g., a knob) is then used to tighten the lace and provide adjustable perpendicular force to the soft tissues. The wearer can continue to tighten the lace until the desired compression has been obtained. Thereafter, the wearer can use the adjustable tensioning mechanism to increase or decrease compression at any time without the need to disengage the strap or connectors.

The orthopedic pressure devices of the disclosure are particularly useful for treating lateral epicondylitis ("tennis elbow"), medical epicondylitis ("golfer's elbow"), carpal tunnel syndrome, patellofemoral syndrome (PFS), chondramalacia patella (CMP), and the like.

For tennis elbow, which occurs at the proximal forearm, the device is positioned as far up the forearm as possible without interfering with elbow flexion and the perpendicular force contact area is positioned centrally over the extensor compartment forearm musculature.

For golfer's elbow located at the upper forearm or for carpal tunnel syndrome located at the distal forearm, the device is positioned as far up the ventral forearm as possible without interfering with elbow flexion and the perpendicular force contact area is positioned centrally with respect to the flexor compartment forearm musculature.

For PFS and CMP, the device is positioned at the lower edge of the patella to provide medial and lateral support.

EMBODIMENTS

1. An orthopedic pressure device comprising:
   (a) a main body configured to contour to the curvature of a portion of a wearer's anatomy;
   (b) an adjustable strap for securing the main body to the wearer; and
   (c) a displacing mechanism disposed at least partially in the main body for applying perpendicular force to the soft tissues of the wearer, the displacing mechanism comprising a lace and tensioning system for adjusting the perpendicular force to the soft tissues.

2. The orthopedic pressure device of embodiment 1 wherein the displacing mechanism comprises a convexly curved flexible finger, and wherein the lace runs over the outer surface of the finger and the finger deflects under the tension when tension is applied to the lace using the tensioning system.

3. The orthopedic pressure device of embodiment 2 wherein the lace crosses over the outer surface of the finger.

4. The orthopedic pressure device of embodiment 2 or embodiment 3 wherein the finger is from about 2.5 cm to about 7.6 cm long.

5. The orthopedic pressure device of embodiment 1 wherein the displacing mechanism comprises a concavely curved flexible finger comprising a first end and a second end, the first end being adjacent to the tensioning mechanism and the second end being attached to the lace; wherein the second end slides along a track and the finger bows as the lace is tightened using the tensioning system.

6. The orthopedic pressure device of embodiment 5 wherein the finger is from about 2.5 cm to about 7.6 cm long.

7. The orthopedic pressure device of embodiment 1 wherein the displacing mechanism converts torque force into linear force using a rigid mechanical positive displacement mechanism.

8. The orthopedic pressure device of embodiment 7 wherein the rigid mechanical positive displacement mechanism comprises a pressure foot rotatably connected to at least one rigid leg; wherein the at least one rigid leg is positioned at an angle of less than 90° when the lace is not tensioned and the at least one rigid leg rotates toward a 90° angle and applies downward force when the lace is tightened using the tensioning system.

9. The orthopedic pressure device of embodiment 7 wherein the rigid mechanical positive displacement mechanism comprises a convexly curved flexible finger and a rigid wedge that slides along a track; wherein the rigid wedge is spring-loaded to return it to a neutral position and the lace pulls the wedge in the opposite direction along the track when tension is applied to the lace using the tensioning system such that the finger deflects applying a downward force.

10. The orthopedic pressure device of embodiment 9 wherein the positive displacement mechanism further comprises a pressure foot that contacts the soft tissue and applies linear downward force.

11. The orthopedic pressure device of any of embodiments 1-10 wherein the main body is a semicircle or truncated semicircle.

12. The orthopedic pressure device of embodiment 11 wherein the main body has a circumference from about 15 cm to about 50 cm.

13. The orthopedic pressure device of any of embodiments 1-12 wherein the main body further comprises padding on at least a portion of its inner surface.

14. The orthopedic pressure device of any of embodiments 1-13 wherein the displacing mechanism further comprises padding where it contacts and applies perpendicular pressure to the wearer's anatomy.

15. The orthopedic pressure device of any of embodiments 1-14 wherein the displacing mechanism further comprises a rotatable or pivoting pressure foot where it contacts and applies perpendicular pressure to the wearer's anatomy.

16. The orthopedic pressure device of any of embodiments 1-15 wherein the main body and displacing mechanism do not apply circumferential pressure to the wearer's anatomy.

17. The orthopedic pressure device of any of embodiments 1-16 wherein the tensioning system comprises a mechanism of release for disengaging the tensioning system.

18. The orthopedic pressure device of any of embodiments 1-17 wherein the main body comprises a lubricious polymer.

19. The orthopedic pressure device of any of embodiments 1-18 wherein the main body is configured to contour the curvature of a portion of a wearer's appendage.

20. The orthopedic pressure device of embodiment 19 wherein the main body is configured to contour a wearer's forearm.

21. The orthopedic pressure device of embodiment 19 wherein the main body is configured to contour a wearer's leg at the lower edge of the patella.

22. The orthopedic pressure device of any of embodiments 1-21 wherein the tensioning system is a rotary tensioning system.

23. The orthopedic pressure device of any of embodiments 1-22 wherein the displacing mechanism can provide at least about 0.6 cm and up to about 2.5 cm of deflection.

24. The orthopedic pressure device of embodiment 1, wherein the main body is a semi-rigid or rigid body.

25. An orthopedic pressure device comprising:
(a) a main body configured to contour to the curvature of a portion of a wearer's anatomy;
(b) an adjustable strap for securing the main body to the wearer; and
a displacing mechanism partially disposed in the main body for applying perpendicular force to the soft tissues of the wearer, the displacing mechanism comprising
a lace and tensioning system for adjusting the perpendicular force to the soft tissues, and
a separable pressure pad where the mechanism contacts and applies perpendicular pressure to the wearer's anatomy.

The complete disclosures of the publications cited herein are incorporated by reference in their entirety as if each were individually incorporated. Various modifications and alterations to this disclosure will become apparent to those skilled in the art without departing from the scope and spirit of this disclosure. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. An orthopedic pressure device comprising:
(a) a main body including an aperture defined therein, the main body configured to contour to the curvature of a portion of a wearer's anatomy;
(b) an adjustable strap for securing the main body to the wearer; and
(c) a displacing mechanism disposed at least partially in the main body for applying perpendicular force to the soft tissues of the wearer, the displacing mechanism comprising a force member at least partially received in the aperture and having structure adapted for contacting the soft tissues, and a lace and a tensioning mechanism disposed at a location on the main body for adjusting the perpendicular force to the soft tissues, wherein at least a portion of the force member is displaced out of the aperture in directions toward the wearer and away from the main body when tension is applied to the lace using the tensioning mechanism, and wherein the location of the tensioning mechanism remains fixed relative to the adjustable strap when tension is applied to the lace using the tensioning mechanism.

2. The orthopedic pressure device of claim 1 wherein the force member comprises a convexly curved flexible finger, and wherein the lace runs over the outer surface of the finger and the finger deflects under the tension when tension is applied to the lace using the tensioning mechanism.

3. The orthopedic pressure device of claim 2 wherein the lace crosses over the outer surface of the finger.

4. The orthopedic pressure device of claim 2 wherein the finger is from about 2.5 cm to about 7.6 cm long.

5. The orthopedic pressure device of claim 1 wherein the force member comprises a concavely curved flexible finger comprising a first end and a second end, the first end being adjacent to the tensioning mechanism and the second end being attached to the lace; wherein the second end slides along a track and the finger bows as the lace is tightened using the tensioning system.

6. The orthopedic pressure device of claim 5 wherein the finger is from about 2.5 cm to about 7.6 cm long.

7. The orthopedic pressure device of claim 1 wherein the displacing mechanism converts torque force into linear force using a rigid mechanical positive displacement mechanism.

8. The orthopedic pressure device of claim 7 wherein the rigid mechanical positive displacement mechanism comprises a pressure foot rotatably connected to at least one rigid leg; wherein the at least one rigid leg is positioned at an angle of less than 90° when the lace is not tensioned and the at least one rigid leg rotates toward a 90° angle and applies downward force when the lace is tightened using the tensioning mechanism.

9. The orthopedic pressure device of claim 7 wherein the rigid mechanical positive displacement mechanism comprises a convexly curved flexible finger and a rigid wedge that slides along a track; wherein the rigid wedge is spring-loaded to return it to a neutral position and the lace pulls the wedge in the opposite direction along the track when tension is applied to the lace using the tensioning mechanism such that the finger deflects applying a downward force.

10. The orthopedic pressure device of claim 9 wherein the positive displacement mechanism further comprises a pressure foot that contacts the soft tissue and applies linear downward force.

11. The orthopedic pressure device of claim 1, wherein the main body is a semicircle or truncated semicircle.

12. The orthopedic pressure device of claim 11 wherein the main body has a circumference from about 15 cm to about 50 cm.

13. The orthopedic pressure device of claim 1, wherein the force member further comprises padding where it is adapted to contacts and apply perpendicular pressure to the wearer's anatomy.

14. The orthopedic pressure device of claim 1, wherein the force member further comprises a rotatable or pivoting pressure foot where it contacts and applies perpendicular pressure to the wearer's anatomy.

15. The orthopedic pressure device of claim 1, wherein the main body and displacing mechanism do not apply circumferential pressure to the wearer's anatomy.

16. The orthopedic pressure device of claim 1, wherein the tensioning mechanism comprises a release for disengaging the tensioning mechanism.

17. The orthopedic pressure device of claim 1, wherein the main body comprises a lubricious polymer.

18. The orthopedic pressure device of claim 1, wherein the main body is configured to contour the curvature of a portion of a wearer's appendage.

19. The orthopedic pressure device of claim 18 wherein the main body is configured to contour a wearer's forearm.

20. The orthopedic pressure device of claim 18, wherein adjusting the tightness of the adjustable strap does not involve applying tension to the lace using the tensioning mechanism.

21. The orthopedic pressure device of claim 1, wherein the tensioning mechanism is a rotary tensioning mechanism.

22. The orthopedic pressure device of claim 1, wherein the displacing mechanism can provide at least about 0.6 cm and up to about 2.5 cm of deflection.

23. The orthopedic pressure device of claim 1, wherein the main body is a semi-rigid or rigid body.

24. An orthopedic pressure device comprising:
  (a) a main body configured to contour to the curvature of a portion of a wearer's anatomy;
  (b) an adjustable strap for securing the main body to the wearer; and
  (c) a displacing mechanism partially disposed in the main body for applying perpendicular force to soft tissues of the wearer that are located underneath the main body when the device is worn, the displacing mechanism comprising
  a displaceable pressure pad adapted to contact and apply downward perpendicular force to the soft tissues underneath the main body, and a lace and a tensioning mechanism for adjusting the perpendicular force applied through the pad to the soft tissues by adjusting the displacement of the pressure pad relative to the main body,
  wherein the lace is coupled to and runs over at least a portion of an outer surface of the pad, wherein at least a portion of the pad is displaced toward the soft tissues and away from the main body when tension is applied to the lace using the tensioning mechanism, and wherein adjusting the tightness of the adjustable strap does not involve applying tension to the lace using the tensioning mechanism.

25. The device of claim 24, wherein the pressure pad includes a skin facing surface that is concavely curved, and wherein the lace runs over a portion of an opposite, outer surface of the pad.

26. The device of claim 24, wherein the main body including an aperture defined therein and the pad is at least partially received in the aperture, and wherein at least a portion of the force member is displaced out of the aperture when tension is applied to the lace using the tensioning mechanism.

* * * * *